United States Patent [19]
Carden, Jr.

[11] Patent Number: 5,405,309
[45] Date of Patent: Apr. 11, 1995

[54] X-RAY EMITTING INTERSTITIAL IMPLANTS

[75] Inventor: John L. Carden, Jr., Tucker, Ga.

[73] Assignee: Theragenics Corporation, Norcross, Ga.

[21] Appl. No.: 53,422

[22] Filed: Apr. 28, 1993

[51] Int. Cl.⁶ .............................................. A61N 5/00
[52] U.S. Cl. ............................................ 600/3; 600/8; 427/5
[58] Field of Search ................................ 600/1–8; 427/2, 3, 5, 98

[56] References Cited

U.S. PATENT DOCUMENTS

| | | | |
|---|---|---|---|
| 3,351,049 | 11/1967 | Lawrence | 600/8 |
| 4,323,055 | 4/1982 | Kubiatowicz | 600/8 |
| 4,702,228 | 10/1987 | Russell, Jr. et al. | |
| 4,891,165 | 1/1990 | Suthanthiran | 600/8 |

FOREIGN PATENT DOCUMENTS 8604248 7/1986 WIPO ..................................... 600/8

Primary Examiner—William E. Kamm
Assistant Examiner—J. P. Lacyk
Attorney, Agent, or Firm—Larson and Taylor

[57] ABSTRACT

Safe, isotopically pure Pd-103-containing seeds of high apparent activity are formed by bombarding an Rh target in a cyclotron with high energy particles to obtain Rh containing carrier-free Pd-103, separating therefrom the carrier-free Pd-103, adding a small amount of Pd to the carrier-free Pd-103, electroplating said Pd-103/Pd admixture to a pellet(s) of electroconductive material and encapsulating the pellet(s) within a biocompatible container or shell.

8 Claims, 1 Drawing Sheet

Fig. 1
Fig. 2
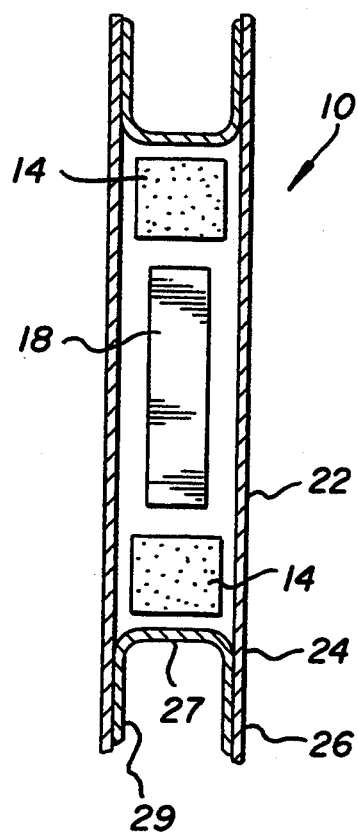
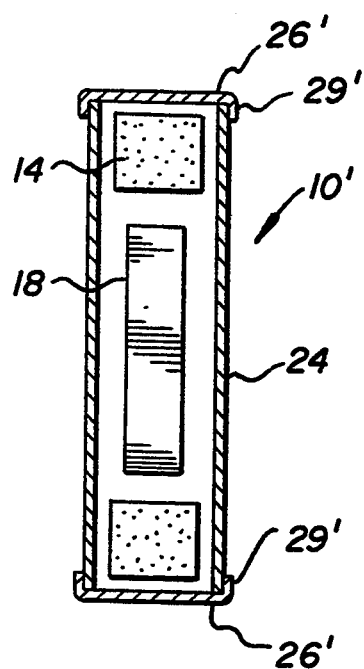

X-RAY EMITTING INTERSTITIAL IMPLANTS

BACKGROUND OF THE INVENTION

1. Field of the Invention

The present invention relates to therapeutic radiation oncology. More particularly, the present invention is directed to a radioactive X-ray source commonly referred to as a seed for interstitial implantation and to its method of manufacture.

2. Description of the Prior Art

Interstitial implantation of radiation-emitting materials for localized tumor treatment has long been recognized. The advantages of interstitial implants reside in their ability to concentrate the radiation on the tumor tissue while minimizing radiation exposure to normal tissue. Commonly used implantable materials include radioactive gold (gold-198) and radon-222. These materials are not without their shortcomings, however, since the highly penetrating radiation they emit not only subject normal tissue to more destructive radiation, but also make it difficult to adequately shield the administering personnel from the radiation emitted.

Another isotope commonly used for seed manufacture is iodine-125. The general effectiveness of these seeds has been described in several publications such as "The Use of Iodine-125 for Interstitial Implants, U.S. Department of Health, Education and Welfare Publication (FDA) 76-8022, Basil Hilaris et al, November 1975 and in U.S. Pat. No. 3,351,049.

U.S. Pat. No. 3,351,049 to Lawrence et al suggests the use of carrier-free palladium 103 as therapeutic seeds. Carrier-free palladium 103 (i.e., palladium 103 which does not contain palladium metal or other palladium isotopes) has never been incorporated in commercially-available tumor-treating materials because its short 17-day half-life makes it difficult to work with in view of the processing time required to isolate and purify the isotope. Perhaps of greater concern is the difficulty in producing a carrier-free palladium 103 seed which is safe in case of a failure of the seed outer container, that is, a seed from which the palladium 103 can not escape from its supporting medium inside the seed and migrate into the blood stream and/or normal tissue of patients treated in the event of such a failure. Numerous articles describe preparation of carrier-free palladium, from cyclotrons as, for example, W. M. Garrison, J. G. Hamilton, U.S. atomic Energy Commission, UCRL-1067 (1950); P. V. Harper, K. A. Lathrop, L. Baldwin, Y. Oda and L. Kryhtal, Pd-103: A New Isotope for Interstitial Implantation at Operation, Annals of Surgery, 148 p. 606 (1958); P. V. Harper, K. A. Lathrop and J. L. Need, source unknown (1961); V. I. Levin et al, Separation of Pd-103 without a Carrier, Otkrytiya, Izobret, 1969, 46(1), 170; V. I. Levin et al, Preparation of Carrier free Palladium-103 and a Radioactive Colloidal Palladium Composition for Medicinal Purposes, Radiokhimiya, 13(4), 622-7 (1971); P. Tarapcik and V. Mikulaj, Separation of Palladium 103 from Cyclotron Irradiated targets, Radiochem. Radioanal. Lett., 48 (1981) 1969, 46. In all instances, however, only small amounts of the isotope have been prepared, and then only for research purposes.

U.S. Pat. No. 4,702,228 does describe therapeutic seeds containing palladium 103 prepared by increasing the Pd-102 content found in palladium metal, i.e., by enriching palladium metal in palladium 102 and then by exposing it to a neutron flux so as to convert a small fraction of the palladium 102 to palladium 103. Seeds prepared in accordance with the process of this patent have been commercially successful, but are not without their shortcomings.

Unlike cyclotron palladium 103 production wherein carrier-free palladium 103 can be produced, nuclear reactor produced palladium 103 is not carrier-free. Palladium 103 is produced in a nuclear reactor by bombarding a target containing Pd-102 with neutrons (Pd-102(n, $\gamma$) Pd-103). Since all of the Pd-102 nuclei are not converted and, since in addition, other naturally occurring isotopes of the element palladium are present in the target, Pd-103 cannot be produced in a carrier free state. In addition, since there are always other isotopes of Pd present, neutron activation products of these isotopes are produced as well. For example, the reaction Pd-108(n, $\gamma$)Pd-109 also occurs and therefore Pd-103 from a reactor is always found in the presence of the radioisotope Pd-109 until the Pd-109 decays out of the matrix. Since Pd-109 is the same element as Pd-103, no chemical means are known to effect their separation. The presence of other nuclides of Pd, also leads to the production of significant activities of certain non-Pd radioisotopes, e.g. Pd-111, which decays to Ag-111, further complicating the radiochemical purification of the Pd-103 matrix. In contrast, carrier-free Pd-103 produced in a particle accelerator such as a cyclotron enters the purification scheme in a far purer state with essentially no unseparable radioisotopes present.

Another drawback of seeds produced in a nuclear reactor from Pd-102 enriched palladium is that for practical reasons soon to be apparent, one is obliged to use reactor produced Pd-103 at the specific activity level generated in the reactor without adjustment while the specific activity of cyclotron produced Pd-103 can be adjusted to provide for its economical utilization while at the same time providing for the production of a seed of predetermined therapeutic or apparent activity.

The specific activity of Pd-103 that can be produced in a nuclear reactor is determined by the enrichment of the Pd-102 target used, the neutron flux in the reactor and the length of exposure of the target to the neutron flux in the reactor. At this time, the highest enrichment of the Pd-102 available (Oak Ridge National Laboratories (ORNL)) has an isotopic purity of 77.9% Pd-102 with the remaining 22.1% made up of the other isotopes of Pd. The highest neutron flux available in the world is found in the ORNL HFIR facility where the level is approximately 2.6E15 neutrons/$cm^2$sec. This reactor runs in 21 day cycles with approximately 3 days between and due to the generation of extraneous isotopes such as Ag-111, the maximum practical irradiation time is two cycles. These factors taken together indicate the maximum specific activity that can be derived from a reactor target is approximately 345 Ci/g.

In contrast, the specific activity of carrier-free Pd-103 is 75,000 Ci/g.

The ability to adjust the specific activity of the Pd-103/palladium mixture onto the support allows the self absorption (the tendency of Pd or other nuclei of high atomic number to adsorb the low energy X-rays produced when a Pd-103 nucleus disintegrates) to be adjusted to a known value thus facilitating the manufacture of a seed with an accurately predetermined therapeutic or apparent activity. Such an adjustment procedure is not practical with reactor produced Pd-103 for two reasons: 1) because its specific activity, which is as illustrated above initially much lower than the carrier free Pd-103 produced in a cyclotron, can only be adjusted downward thereby increasing the amount Pd-103 and, because they are inseparable chemically, the amount of enriched Pd-102 that must be used per seed contrary to the best economic practice of the process and contrary to the conservation of the difficulty replaceable enriched Pd-102 and 2) the addition of palladium metal to reactor produced Pd-102 lowers the enrichment level of the Pd-102 contained in the seeds produced thereby reducing the utility of the Pd-102/palladium mixture recovered from unused seeds, an essential element in the economical utilization of the enriched Pd-102 resource.

In view of the amounts of contaminating Pd-isotopes and non-Pd-isotopes present in Pd-103 produced in a nuclear reactor from Pd-102 enriched Pd and the constantly varying factors involved, e.g. neutron flux, extent of Pd-102 enrichment, exposure time, etc., it is difficult, if not impossible, to predict what the purity and/or specific activity of the resulting Pd-103 product will be for any given production run. Thus, Pd-103 production processes employing Pd-102 enriched Pd do not lend themselves to the design of a process for production of a reproducible product of predetermined activity.

A further shortcoming in seeds produced from Pd-102 enriched Pd resides in the fact that large amounts of Pd-nuclei remain which tend to shield the low energy X-rays released when the Pd-103 nuclei disintegrate. The practical result of this is that additional palladium material containing enriched Pd-102 and Pd-103 must be used to compensate for the X-rays absorbed by the palladium nuclei to attain the desired X-ray intensity outside the interstitial implant device.

Lastly, reactor produced Pd-103 from Pd-102 enriched Pd not only is costly because of the difficulty in enriching Pd metal in Pd-102, but poses environmental problems. Producing Pd-103 with a reactor requires the fission of uranium to produce the required neutrons. An adequate means to dispose of the resulting transuranic waste is still a subject of debate. The larger amounts of contaminant isotopes produced in a reactor target also present a disposal problem. Since electric power is the only requirement to make a cyclotron function and contaminant isotope production is much less, cyclotron produced Pd-103 has far less of an environmental impact.

It is apparent therefore that if it were possible to produce a seed of Pd-103 of sufficient purity and desired therapeutic activity via the cyclotron route that was also safe, that the advantages it would present over the presently commercially available Pd-103 seeds would be of immeasurable value.

It is an object of the invention, therefore, to provide a seed of Pd-103 of high isotopic purity and desired therapeutic activity that is also safe for use as an interstitial implant. By the term "safe" as used herein and in appended claims is meant a seed characterized by being non-toxic and having radioisotopically pure Pd-103 bonded to the support carrying same in a manner that preclude release therefrom, thereby substantially reducing the chances of the radioactive isotope leaking into the circulatory system of the patient.

Another object of the invention is to provide an interstitial seed composed of carrier free Pd-103 having added to it small amounts of palladium metal, which seed has an isotopic purity such that the ratio of the radiation absorbed dose to the patient from isotopes other than Pd-103 to that from Pd-103 is less than 0.01 and a specific activity of at least 2.5 Ci/gm.

A further object of the present invention is to provide a process for the production of a safe, Pd-103-containing seed substantially reduced in the self-shielding properties that characterize commercially-available Pd-103 seeds and which therefore enables use of smaller amounts of Pd-103 to achieve the desired X-ray intensity (therapeutic or apparent activity).

Yet another object of the invention is to provide a process for the production of Pd-103 seeds which does not present the purification difficulties encountered in present commercially available Pd-103 production processes.

A further object of the invention is to provide a process for the reproducible production of safe Pd-103 containing seeds of predetermined isotopic purity, self-shielding and therapeutic or apparent activity.

Lastly, the invention provides a process for Pd-103 seed production that is cheaper, does not require a difficulty replaced resource (enriched Pd-102) and that poses a reduced threat to the environment.

SUMMARY OF THE INVENTION

These and other objects of the invention are obtained by a process which comprises preparing a seed that is safe for implantation into a tumor within a living body to emit x-ray radiation, said seed having a predetermined radiation level measured as apparent mCi comprising irradiating an Rh metal target in a charged particle accelerator under conditions that produce carrier-free Pd-103 within said Rh metal target in a charged particle accelerator under conditions that produce carrier-free Pd-103 within said Rh metal, recovering carrier-free Pd-103 from the rhodium metal, adding palladium metal to said carrier-free Pd-103 in a small amount sufficient to promote electroplating of said mixture and to obtain the desired level of self shielding, removing non-palladium isotopes from said admixture, if necessary, electroplating a layer of said Pd-103/palladium admixture having a known specific activity and self absorption onto at least one pellet of an electroconductive material substantially non-absorbing of X-rays, the amount of Pd-103 in said layer being sufficient to provide a radiation level measured as apparent mCi of greater than 0.5, and encapsulating said at least one pellet within a shell of a biocompatible material that is penetrable by X-rays in the 20–23 kev range.

In another aspect of the invention there is obtained a safe seed for implantation into a tumor within a living body to emit x-ray radiation said seed having a predetermined radiation level measured as apparent mCi comprising irradiating a rhodium metal target in a charged particle accelerator under conditions that produce carrier-free Pd-103 in said rhodium metal, recovering carrier-free Pd-103 from rhodium metal, adding palladium metal to said carrier-free Pd-103 in a small amount sufficient to promote electroplating of said mixture and to obtain the desired level of self shielding, removing, if necessary, non-palladium isotopes from said admixture electroplating a layer of said Pd-103/palladium admixture having a known specific activity and self absorption onto at least one pellet of an electroconductive material substantially non-absorbing of X-rays, the amount of Pd-103 in said layer being sufficient to provide a radiation level measured as apparent mCi of greater than 0.5, and encapsulating said at least one pellet within a shell of a bicompatible material that is penetrable by X-rays in the 20–23 kev range.

In yet another aspect of the invention, there is provided a seed for safe implantation into tumors which consists of a layer of carrier free Pd-103 having added thereto Pd in an amount that provides a seed having an isotopic purity such that the ratio of the radiation absorbed dose to the patient from isotopes other than Pd-103 to that from Pd-103 is less than 0.01 and a specific activity of at least 2.5 Ci/gm electroplated onto an electroconductive support, the amount of said Pd being sufficient to promote said electroplating, said at least one electroplated pellet containing Pd-103 in an amount sufficient to provide a radiation level measured as apparent mCi of greater than 0.5, and a shell of a bicompatible material encapsulating said at least one electroplated pellet, said biocompatible material being penetrable by X-rays in the 20–23 kev range.

By the term isotopic purity as used herein and in the appended claims is meant the proportion of the total radiation absorbed dose due to the specified nuclide, that is, that the dose from other isotopes is less than 1.0% of the Pd-103 dose.

By the term specific activity as used herein and in the appended claims is meant the total activity of the Pd-103 per gram of the admixture with palladium metal.

By the term "therapeutic or apparent activity" as used herein and the appended claims is meant the Pd-103 activity as determined from measuring the X-ray intensity outside the seed. This is also the therapeutic activity, i.e. the activity that actually kills the cancer and therefore the activity the doctor must use when developing a plan for treating the patient.

BRIEF DESCRIPTION OF THE DRAWINGS

FIG. 1 is a cut-away view of an implantable X-ray emitting capsule or seed, embodying various features of the present invention; and FIG. 2 is a cut-away view of an alternative embodiment of an implantable seed.

DESCRIPTION OF THE PREFERRED EMBODIMENTS

With reference to the drawings, a seed or capsule 10, embodying features of the invention is implanted at a selected site within a living body and emits localized X-ray radiation therein. The X-rays are emitted from a pair of pellets 14 of generally cylindrical shape of electroconductive material having electroplated thereon the carrier-free Pd-103/Pd admixture of the present invention. Positioned between the two pellets is a rod-shaped marker 18 formed of X-ray-opaque material that provides a means of visualizing the seed 10 with external X-ray equipment after the seed has been implanted in the body.

In accordance with the present invention, a target for use in the charged particle accelerator is prepared by depositing rhodium metal onto a suitable substrate such as a copper or a silver substrate. The rhodium target thus prepared is then placed in a charged particle accelerator such as a cyclotron and bombarded with protons or deuterons. The energy of the impacting particle is chosen so that for all practical purposes the only Pd atoms created on the rhodium target are Pd-103, that is, the Pd-103 is carrier-free. The rhodium metal containing the carrier-free Pd-103 is then placed in a hot cell wherein the rhodium metal is removed from the substrate by, for example, etching away with $HNO_3$. This removal is preferably accomplished by mechanically disrupting the continuity of the rhodium layer on the substrate as by perforating the surface with a sharply pointed impact tool. The exposed (i.e. non-deposit-containing) substrate surface is covered to protect it and the perforated target immersed in a $HNO_3$ bath. A solution containing rhodium flakes results, which is filtered to recover the solid rhodium flakes containing Pd-103. The recovered rhodium flakes are rinsed on the filter and the flakes together with the filter placed in a crucible and heated to decompose the filter leaving the rhodium metal flakes containing the Pd-103.

The rhodium metal flakes thus obtained are then partially dissolved in molten $NaHSO_4$ and the resulting $NaHSO_4$/rhodium flake mixture is dissolved in dilute HCl which provides soluble rhodium salts dissolved in dilute HCl. This procedure is normally repeated several times so as to dissolve any remaining rhodium metal containing carrier-free palladium-103.

Palladium is then added (usually in the form of a soluble salt such as $PdCl_2$) to the solution containing rhodium salts. Although palladium has a high atomic number and would normally be considered an undesirable additive to a low energy X-ray emitting seed, its addition in accordance with the present invention, has been found to be essential and advantageous in several respects. Foremost, the added palladium promotes the subsequent electroplating and ensures strong adhesive of the Pd-103/Pd mixture to the support therefor, thereby forming a physiologically inert layer which will not allow the radioactive Pd-103 to be mobilized into the circulation of a human should the titanium outer shell be breached and body fluids allowed to come into contact with the Pd-103 containing layer.

Secondly, the addition of palladium metal represents the ability to adjust the specific activity of the Pd-103/palladium mixture electroplated onto the support with the objective of adjusting its self absorption to a known value thus facilitating the manufacture of a seed with an accurately predetermined therapeutic or apparent activity. Thirdly, if further purification of the carrier-free Pd-103 is necessary, the presence of the Pd reduces loss of Pd-103 occurring during said purification. Lastly, the Pd addition can be used to provide a final product having a desired specific activity and consequently a predetermined self absorption in the electroplated layer containing the Pd-103.

The amount of palladium added, therefore, will vary depending principally upon the amount of Pd-103 available. Normally, no more than about 0.000075 grams of palladium per pellet are necessary to provide an electroplate layer from which the isotope does not escape. Generally, the amount of palladium metal added falls in the range of 0.00005 to 0.0005 grams per pellet.

If trace amounts of non-Pd isotopes are present in the solution containing soluble rhodium salts, these are removed at this stage of the process by the following purification procedures:

The solution containing soluble rhodium salts and Pd-103 is then passed through an anion resin exchange column wherein palladium in the form of $PdCl_4^{2-}$ attaches to the column and $Rh^{3+}$ passes through. Other trace isotopes comprised of elements such as Ru, Co, Zn and the like can then be eluted off the column using hydrochloric acid of different acid strengths for various groups of such elements.

Finally, the mixture of Pd-103 and Pd is eluted off the column with $NH_4OH$ as palladium amine complex and the palladium amine complex is electroplated onto a suitable electroconductive support.

The electroconductive support onto which the Pd-103 containing complex of the invention is electroplated is preferably in the form of a pellet and can be constructed of any non-toxic, electroconductive material composed of low atomic number so as to minimize internal absorption of the X-ray radiation. The pellet can be of any desired shape, but is preferably cylindrical. Examples of suitable supports are those made of carbon, normally in the form of graphite and aluminum.

Of these supports, the preferred support is graphite in the form of cylindrical pellets.

The amount of Pd-103 in pellet 14 depends upon the radiation dosage required for each seed. For a seed having the configuration shown in FIG. 1, pellets having a diameter of 0.023 inch will have a layer of the Pd-103/Pd admixture that preferably contains a specific activity of at least 2.5 Ci/g. The total radiation level emitted by both pellets is more accurately expressed as an apparent value in mCi which takes into account the self-absorption within the layer of the Pd-103/Pd admixture. By adjusting the specific activity of the Pd-103/Pd admixture and the amount of this admixture plated onto the pellets, the apparent activity level of the seed can be adjusted to between about 0.5 to 300 mCi/seed.

The opaque marker 18 is generally comprised of a high atomic number element which, as a result of its high atomic number, is X-ray opaque. Suitable examples of such elements include lead and rhodium.

The shell 22 encapsulates the pellets 14 and the opaque marker 18 in such a way that the admixture of radioactive Pd-103/Pd cannot under normal circumstances come into contact with body tissue or fluids due to this encapsulating shell, thereby forming an additional barrier to escape and distribution of the radioactive isotope throughout the body. Accordingly, the outer shell is formed of a material that is biocompatible and preferably the encapsulating shell is titanium. The wall thickness of the titanium shell is about 0.001 to 0.005 inch, preferably 0.002 inch.

Most advantageously, the shell will take the form of a tube with the ends thereof closed in a manner that precludes direct contact between body tissue and fluids and the internal components of the seed. This closure of the ends can be effected, for instance, by swaging shut the open ends and welding. Alternatively, the ends may be closed by capping them in a suitable manner, a preferred example of which is shown in FIG. 1 and FIG. 2. Referring to these figures, it is seen that the outer shell 22 is constructed from a three piece assembly, including the tube 24 and the pair of end caps 26 that are welded to the tube 24 after the other components, i.e., the X-ray-emitting pellets 14 and the X-ray-opaque marker 18 are inserted into the tube. The important advantage of this construction relative to the construction of the shells of seeds, some presently in commercial production, is that it permits the formation of thinner ends, i.e., about the same thickness as the sidewalls, and thereby provides for a better angular distribution of the emitted X-rays. Even though the shell material is selected to be as transparent to X-rays as is consistent with other requirements of the shell material, the shell will absorb some of the low-energy X-rays emitted by the palladium-103. By using end caps 26 having the same thickness as the tube 24, the end of the shell 22 is as thick as the sidewalls of the shell, promoting the generally isotropic angular distribution of X-rays from the seed. In the seed illustrated in FIG. 1, the end caps are cup-shaped, including a circular end wall 27 and an outwardly extending cylindrical sidewall 29. The diameter of the end caps 25 is proportioned to fit closely within the ends of the tube of the seed. After the seed 1 is assembled, the end caps 26 are welded, e.g., with a laser, to the tube 24, thereby permanently sealing the pellets 14 and the marker 18 within the shell. Although this construction produces double-walled sections extending outwardly of the circular end walls 27 of the end caps; a double-walled thickness is less than the thickness of end beads in some currently produced seeds, and the double-walled segment results in additional shielding only along a narrow angular region.

FIG. 2 illustrates an alternative embodiment of a seed 10', in which end caps 26' having side walls 29' are proportioned to overfit the walls of tube 24 and welded thereto. Otherwise, the pellets 14, markers 18 and tube 24 are as described in the FIG. 1 embodiment.

The following example is included to further illustrate the invention, but is to be considered as exemplary only and as not limiting of the invention in any way.

EXAMPLE

Approximately 2 grams of rhodium metal are deposited on a copper substrate to provide a cyclotron target. The target thus prepared is placed in a cyclotron and bombarded with protons having an energy of 14 million electron volts for a period of 160 hours to provide Rh containing carrier-free Pd-103. The Pd-103 containing Rh deposit is removed from the copper substrate and the Pd-103/Pd mixture of the invention recovered using the following procedure.

Remove Rh deposit from copper substrate

Perforate the Rh deposit by mechanically etching with a small electric engraving tool.

Briefly dip the target into a vessel containing enough 6N $HNO_3$ to cover the target.

Withdraw the target and rinse with DI water to remove the $HNO_3$. Dry the target.

Cover the copper surfaces of the target with a chemically inert material so that only the Rh surface is exposed.

With only the Rh surface exposed, return the target to the vessel containing $HNO_3$ and etch until all the Rh is removed.

Pass the acid solution through a filter funnel containing ashless filter paper catching the Rh fragments in the filter.

Rinse the filter with small portions of deionized (DI) water to remove any residual Cu ions.

Dissolve Rh foil

Place filter paper into a quartz crucible and gently push it to the bottom with a tamping rod. Place the crucible into a crucible furnace and heat at 700° C. until only a thin white ash remains from the filter paper. This operation should require approximately 30 min.

Remove crucible from furnace and allow to cool to near ambient.

Carefully transfer 30 grams of $NaHSO_4$ into the crucible using a powder funnel.

Slowly place crucible with lid in place into crucible furnace at 700° C. Heat for 90 min. watching carefully during the first 5 minutes to control boiling if necessary.

Remove crucible from furnace and allow to cool to near ambient.

To the crucible, add 20 ml of hot 1M HCl and stir until the solidified mass breaks free. Carefully transfer the solution and solid residue to a 250 ml beaker containing a magnetic stirring bar.

Rinse the crucible with 10 ml portions of 1M HCl to dissolve any residual solid and add rinses to the beaker.

Stir with gentle heating (keep well below the boiling point) until all solids are dissolved.

Taking care not to transfer the stirring bar, pour the contents of the beaker into a filter apparatus containing ashless filter paper retaining both the solid (Rh remaining to be dissolved) and filtrate (dissolved Rh and Pd-103). Rinse the beaker with small portions of 1M HCl and pass these through the filter. Finally, rinse the filter with small portions of 1M HCl adding this to the filtrate. If solid remains in the filter, return the filter to the quartz crucible and repeat all intervening steps until all Rh fragments are dissolved.

Assay the filtrate for Pd-103 activity and add a volume of $PdCl_2$ solution to the filtrate such that at least 5 mg of Pd carrier is added; the exact amount added depending on the specific activity of Pd-103 desired.

Set up a gravity filter funnel with No. 2 Whatman paper. Add one ml 0.1M $AgNO_3$ to the filtrate, slowly mix, and pour through the filter. Rinse both beaker and filter with DI water.

Prepare an anion exchange column containing approximately 30 ml of resin in the chloride form and a glass wool retaining plug on top of the resin bed.

Slowly pour the Rh solution into a reservoir on top of the column. Wash the transfer beaker 3 times with small portions of 0.1M HCl and add to the reservoir. Open the stopcock and allow the solution to flow through the column with an elution rate of approximately 6 drops per second until the liquid level reaches the top of the glass wool plug above the resin bed.

Pass the following solutions through the column at a flow rate of approximately 6 drops per sec.

0.03M HCl 4 m HCl

DI water. Save this fraction for possible Pd recovery.

Concentrated $NH_4OH$. Elute Pd into a clean 400 ml beaker at a flow rate of 6 drops per second.

DI water. Combine this wash with the $NH_4OH$. Make the $NH_4OH$/water rinse solution to volume and assay for Pd-103 and trace isotope activity. The specific activity can be calculated from the activity of Pd-103 and mass of Pd added.

High purity graphite rods having a diameter of about 0.023 inch are cut to a length of approximately 0.035 to form pellets. The graphite pellets are electroplated with the above solution of palladium amine complex to which has been added ammonium chloride and nicotinamide as a plating additive. The electroplating procedures employ ordinary direct electroplating technology. The resulting layer of Pd-103/Pd on each graphite pellet 13 can provide an apparent seed activity of between 0.5 and 300.

ASTM B265-78, grade 2 titanium is used to form tabular sections, 0.177 in. in length, 0.032 in. in outside diameter and 0.028 in. inside diameter (0.002 in. wall thickness). The same titanium is used to form end caps, 0.027 in. long, OD 0.028 in., ID 0.024 in., wall thickness (including end walls) of 0.002 in.

The seed is constructed by inserting two pellets 14 in the tube 24 segment, flanking a marker 18 formed of a lead rod segment, inserting the caps in the ends of the tube and laser-welding the end caps to the tube.

The advantages offered hereto by commercially available Pd-103 seeds over other isotopes interstitially implanted such as iridium-192, gold-198 or radon-222 and iodine-125 is well documented. Unlike these isotopes, Pd-103 seeds do not emit high energy gamma rays and the energy of its X-ray radiation is lower. Consequently, the action of Pd-103 radiation is more localized within a tumor, does little damage to surrounding tissue and is highly attenuated within the body. A Pd-103 seed prepared according to the present invention offers all of these same advantages and, in addition, isotopically pure seeds using smaller amounts of Pd-103 since the specific activity of the Pd-103/Pd admixture used in their production can be adjusted to minimize the self-absorbing properties of the electroplated layer. An additional advantage over previously available Pd-103 seeds is the possibility of, by taking advantage of the adjustable specific activity of Pd-103 afforded by this invention to produce seeds of much higher (at least a factor of times 3) apparent activity than previously possible.

The small size of the Pd-103 seed of the present invention allows them to be permanently implanted with a minimum of tissue trauma. They may be injected through a #17 gauge needle or may be implanted using established applicators such as Scott, Mick or Henschke applicators. Once implanted, they can be left there indefinitely, thereby reducing the risk of infection, radiation exposure and surgical complications that often accompany removable implants.

While the invention has been described in terms of certain preferred embodiments, modification obvious to one of ordinary skill in the art may be made without departing from the scope of the invention.

What is claimed is:

1. A seed for implantation into a tumor within a living body to emit X-ray radiation thereto comprising at least one pellet of an electroconductive support substantially non-absorbing of X-rays, having electroplated thereon a layer of a palladium composition consisting of carrier-free palladium 103 having added thereto palladium metal in an amount sufficient to promote said electroplating, said at least one electroplated pellet containing Pd-103 in an amount sufficient to provide a radiation level measured as apparent mCi of greater than 0.5, and a shell of a bicompatible material encapsulating said at least one electroplated pellet, said biocompatible material being penetrable by X-rays in the 20–23 kev range.

2. An implantable seed according to claim 1 wherein the electroconductive support comprises graphite.

3. An implantable seed according to claim 1 wherein said seed includes an X-ray opaque marker with said shell for external visualization of said pellet after its implantation in the body.

4. An implantable seed according to claim 3 wherein the material forming said X-ray-opaque marker is selected from the group consisting of lead, rhodium and palladium.

5. An implantable seed according to claim 3 wherein said shell has a generally tubular configuration, said marker is generally centrally located, and said at least one pellet includes two pellets, with one pellet disposed on either side of said marker to help promote a generally isotropic distribution of X-rays emitted from said particle.

6. A seed according to claim 1 wherein the palladium composition possesses a radioisotopic purity such that the dose from other isotopes is less than 1% of that from said Pd-103 and a specific activity of at least 2.5 Ci/g.

7. A seed according to claim 1 wherein the shell is made of titanium.

8. A method of preparing a safe seed for implantation into a tumor within a living body to emit x-ray radiation said seed having a predetermined radiation level measured as apparent mCi comprising irradiating and Rh metal target in a charged particle accelerator under conditions that produce carrier-free Pd-103 in said Rh metal, recovering carrier-free Pd-103 from Rh metal, forming a carrier-free Pd-103/palladium admixture by adding palladium metal to said carrier-free Pd-103 in a small amount sufficient to promote electroplating of said mixture and to adjust its specific activity, removing, if necessary, non-palladium isotopes from said admixture, electroplating a layer of said palladium 103/palladium admixture having a known specific activity and self absorption onto at least one pellet of an electroconductive material substantially non-absorbing of X-rays, the amount of Pd-103 in said layer being sufficient to provide a radiation level measured as apparent mCi of greater than 0.5, and encapsulating said at least one pellet within a shell of a bicompatible material that is penetrable by X-rays in the 20-23 kev range.

* * * * *